United States Patent
Shao et al.

(10) Patent No.: US 10,426,428 B2
(45) Date of Patent: Oct. 1, 2019

(54) METHOD FOR DATA ANALYSIS AND PROCESSING OF AN ELASTICITY DETECTION DEVICE, AND ELASTICITY DETECTION DEVICE

(71) Applicant: WUXI HISKY MEDICAL TECHNOLOGIES CO., LTD., Wuxi (CN)

(72) Inventors: Jinhua Shao, Wuxi (CN); Jin Sun, Wuxi (CN); Houli Duan, Wuxi (CN)

(73) Assignee: WUXI HISKY MEDICAL TECHNOLOGIES CO., LTD., Jiangsu (CN)

(*) Notice: Subject to any disclaimer, the term of this patent is extended or adjusted under 35 U.S.C. 154(b) by 0 days.

(21) Appl. No.: 15/660,900

(22) Filed: Jul. 26, 2017

(65) Prior Publication Data

US 2017/0319170 A1 Nov. 9, 2017

Related U.S. Application Data

(63) Continuation of application No. PCT/CN2015/081937, filed on Jun. 19, 2015.

(30) Foreign Application Priority Data

Feb. 12, 2015 (CN) .......................... 2015 1 0076909

(51) Int. Cl.
*A61B 8/08* (2006.01)
*G06F 16/48* (2019.01)
*A61B 8/00* (2006.01)

(52) U.S. Cl.
CPC ................ *A61B 8/085* (2013.01); *A61B 8/08* (2013.01); *A61B 8/485* (2013.01); *A61B 8/565* (2013.01); *G06F 16/48* (2019.01)

(58) Field of Classification Search
CPC ........ G16H 30/00; G16H 10/00; G16H 40/00; G16H 50/00; A61B 8/565; A61B 8/08; A61B 8/485; A61B 8/085; G06F 16/48
See application file for complete search history.

(56) References Cited

U.S. PATENT DOCUMENTS

2004/0230458 A1* 11/2004 Takayama ............. G06F 19/326 705/3
2006/0026040 A1* 2/2006 Reeves ................. G06F 19/321 705/3

(Continued)

FOREIGN PATENT DOCUMENTS

CN 102043893 A 5/2011
CN 102485435 A 6/2012

(Continued)

OTHER PUBLICATIONS

International Search Report of corresponding International PCT Application No. PCT/CN2015/081937, dated Nov. 11, 2015.

(Continued)

*Primary Examiner* — Bo Joseph Peng
(74) *Attorney, Agent, or Firm* — J.C. Patents

(57) ABSTRACT

Provided is a method for data analysis and processing of an elasticity detection device, and an elasticity detection device. The method includes: transmitting, by each elasticity detection device, a detection result to a cloud server if a communication connection between the elasticity detection device and the cloud server is determined to be normal so that the cloud server can store the detection result in a database. The elasticity detection device transmits a data analysis request to the cloud server, and the cloud server obtains from the database data to be analyzed corresponding to an analysis keyword, analyzes the data to be analyzed to obtain an analysis result, and transmits the analysis result to the elasticity detection device. Thus, the elasticity detection (Continued)

device can obtain a comprehensive and accurate analysis result for different analysis requirements by means of storage and analysis capability of the cloud server on massive detection results.

9 Claims, 6 Drawing Sheets

(56) References Cited

U.S. PATENT DOCUMENTS

| | | | |
|---|---|---|---|
| 2010/0056877 A1 | 3/2010 | Fein et al. | 600/301 |
| 2012/0124287 A1* | 5/2012 | Shibayama | G06F 3/0608 |
| | | | 711/114 |
| 2014/0094701 A1 | 4/2014 | Kwartowitz et al. | 600/438 |
| 2014/0288425 A1* | 9/2014 | Shin | A61B 8/485 |
| | | | 600/438 |
| 2014/0337007 A1* | 11/2014 | Waibel | G06F 17/289 |
| | | | 704/3 |

FOREIGN PATENT DOCUMENTS

| | | |
|---|---|---|
| CN | 102904932 A | 1/2013 |
| CN | 104055539 A | 9/2014 |
| CN | 104337550 A | 2/2015 |
| CN | 104350499 A | 2/2015 |
| CN | 204147059 U | 2/2015 |
| CN | 104622513 A | 5/2015 |
| CN | 104636622 A | 5/2015 |
| EP | 2 832 299 A2 | 2/2015 |
| JP | 2001-104253 A | 4/2001 |
| JP | 2003-233674 A | 8/2003 |
| WO | WO 2013/055795 | 4/2013 |
| WO | WO 2014/113681 A1 | 7/2014 |

OTHER PUBLICATIONS

Chinese First Examination Report of corresponding Chinese patent Application No. 201510076909.X, dated Jun. 3, 2016.
The Japanese Examination Report of corresponding Japan patent application No. 2017-541937, dated Aug. 28, 2018.
Meir, Arie et al., "Distributed Network, Wireless and Cloud Computing Enabled 3-D Ultrasound; a New Medical Technology Paradigm" Plos One; vol. 4, No. 11; (Nov. 2009); pp. e7974-1-e7974-8.
The extended European Search Report of corresponding European patent application No. 15881700.7-1124/32574444, dated Sep. 20, 2018.
The Brazilian Examination Report of corresponding Brazil patent application No. 112017017316-6, dated Oct. 1, 2018.

* cited by examiner

METHOD FOR DATA ANALYSIS AND PROCESSING OF AN ELASTICITY DETECTION DEVICE, AND ELASTICITY DETECTION DEVICE

CROSS-REFERENCE TO RELATED APPLICATIONS

This application is a continuation of International Application No. PCT/CN2015/081937, filed on Jun. 19, 2015, which claims the priority benefit of China Patent Application No. 201510076909.X, filed on Feb. 12, 2015. The contents of the above identified applications are incorporated herein by reference in their entireties.

TECHNICAL FIELD

The present invention relates to the field of data processing technology, in particular to a method for data analysis and processing of an elasticity detection device, and an elasticity detection device.

BACKGROUND

The elasticity of biological tissue has a close relation to the characteristics of a lesion, and has an important reference value for the diagnosis of diseases. In recent years, with the development of elastic imaging technology, a variety of elasticity detection devices for elasticity detection of viscoelastic medium such as human body have been widely used.

At present, a certain elasticity detection device is used by different people to detect the elasticity of their viscoelastic medium organs such as a liver. Taking a detection performed on a certain person as an example, the result of elasticity detection performed on the person i.e., displacement of the viscoelastic medium is stored locally, so that the person's health condition can be determined according to the locally stored detection result after the completion of the detection. Thus, the elasticity detection device is able to determine the health condition of each individual according to each individual's detection result which is stored locally after the detection is performed by the elasticity detection device.

However, it is in high likelihood that there will be a plurality of elasticity detection devices provided in a hospital, and a same person is likely to have used different elasticity detection devices at different times for elastic tests on an organ. At this time, since each elasticity detection device can only obtain the detection data stored locally in itself, the determination for this person's health condition can only be based on an analysis result of the locally stored detection result, which renders the analysis result neither comprehensive nor accurate.

SUMMARY

In view of the problems mentioned above, the present invention provides a method for data analysis and processing of an elasticity detection device and an elasticity detection device so as to overcome the drawback in the prior art that data analysis performed only according to the detection result stored locally by each elasticity detection device results in inaccurate and incomplete analysis results.

According to a first aspect of the present invention, a method for data analysis and processing of an elasticity detection device is provided. The elasticity detection device includes an excitation device for generating an elastic shear wave in a viscoelastic medium of a subject; a capturing device for obtaining a detection result generated by the viscoelastic medium under an action of the elastic shear wave. The method for data analysis and processing of an elasticity detection device includes the following steps:

Determining whether a communication connection between the elasticity detection device and a cloud server is normal;

if the communication connection is normal, transmitting, by the elasticity detection device, the detection result to the cloud server so that the cloud server stores the detection result into a database of the cloud server;

transmitting, by the elasticity detection device, to the cloud server a data analysis request for instructing the cloud server to obtain from the database first data to be analyzed corresponding to an analysis keyword, and analyze the first data to be analyzed to obtain a first analysis result; wherein the first data to be analyzed includes the detection result corresponding to the analysis keyword among all detection results of the elasticity detection device; and receiving and presenting, by the elasticity detection device, the first analysis result transmitted by the cloud server.

In a first possible implementation form of the first aspect, after it is determined that the communication connection between the elasticity detection device and the cloud server is normal, the method further includes:

receiving and storing, by the elasticity detection device, an offline data packet transmitted by the cloud server, the offline data packet being determined by the cloud server according to attribute information of the elasticity detection device.

According to the first possible implementation form of the first aspect, in a second possible implementation form of the first aspect, the method further includes:

obtaining, by the elasticity detection device, second data to be analyzed corresponding to the data analysis request, from the offline data packets, and analyzing the second data to be analyzed to obtain a second analysis result, wherein the second data to be analyzed includes a detection result corresponding to an analysis keyword among all detection results of the elasticity detection device included in the offline data packet.

According to the second possible implementation form of the first aspect, in a third possible implementation form of the first aspect, the method further includes:

performing, by the elasticity detection device, the step of obtaining the second data to be analyzed corresponding to the data analysis request from the offline data packet and analyzing the second data to be analyzed to obtain the second analysis result, if it is determined that the communication connection between the elasticity detection device and the cloud server is not normal.

According to the first aspect, and the first, the second or the third possible implementation form of the first aspect, in a fourth possible implementation form of the first aspect, the data analysis request includes the analysis keyword, the analysis keyword includes at least one of the following information:

individual attribute information of the subject, disease attribute information of the subject, group attribute information of the subject, and attribute information of the elasticity detection device.

According to a second aspect of the present invention, another method for data analysis and processing of an elasticity detection device is provided. The elasticity detection device includes an excitation device for generating an elastic shear wave in a viscoelastic medium of a subject; a capturing device for obtaining a detection result generated by the viscoelastic medium under an action of the elastic shear wave; the method for data analysis and processing of an elasticity detection device includes the following steps:

receiving, by the cloud server, the detection result transmitted by the elasticity detection device, the detection result being transmitted when it is determined that the communication connection the elasticity detection device and the cloud server is normal;

storing, by the cloud server, the detection result into a database;

receiving, by the cloud server, a data analysis request transmitted by the elasticity detection device;

obtaining, by the cloud server, first data to be analyzed corresponding to the analysis keyword from the database according to the data analysis request and analyzing the first data to be analyzed to obtain a first analysis result; wherein the first data to be analyzed includes a detection result corresponding to the analysis keyword among all detection results of the elasticity detection device; and transmitting, by the cloud server, the first analysis result to the elasticity detection device.

In a first possible implementation form of a second aspect, before the cloud server stores the detection result in a database, the method further includes:

obtaining, by the cloud server, historical detection data of the subject from the database according to the subject's individual attribute information included in the detection result, the historical detection data including historical detection results of the viscoelastic medium;

determining, by the cloud server, whether the detection result matches the historical detection data according to a preset rule.

According to the first possible implementation form of the second aspect, in a second possible implementation form of the second aspect, the method further includes:

if the detection result does not match the historical detection data, correcting, by the cloud server, the detection result according to the historical detection data, storing corrected detection result in the database, and feeding back a prompt message to the elasticity detection device, the prompt message is to indicate that the detection result does not match the historical detection data.

In a third possible implementation form of the second aspect, the method further includes:

determining, by the cloud server, an offline data packet corresponding to the elasticity detection device according to the attribute information of the elasticity detection device;

transmitting, by the cloud server, the offline data packet to the elasticity detection device; the offline data packet is used so that the elasticity detection device can obtain from the offline data packet second data to be analyzed corresponding to the data analysis request and analyze the second data to be analyzed to obtain a second analysis result, the second data to be analyzed including a detection result corresponding to the analysis keyword among all detection results of the elasticity detection device included in the offline data packets.

According to the third possible implementation form of the second aspect, in a fourth possible implementation form of the second aspect, the determining, by the cloud server, an offline data packet corresponding to the elasticity detection device according to the attribute information of the elasticity detection device includes:

determining, by the cloud server, identification information matching the attribute information of the elasticity detection device among the identification information of at least one offline data packet generated in advance;

obtaining, by the cloud server, an offline data packet corresponding to the matched identification information.

According to the third possible implementation form of the second aspect, in a fifth possible implementation form of the second aspect, the determining, by the cloud server, an offline data packet corresponding to the elasticity detection device according to the attribute information of the elasticity detection device includes:

receiving, by the cloud server, a request for downloading the offline data packet transmitted by the elasticity detection device, the download request including the attribute information of the elasticity detection device; and generating, by the cloud server, the offline data packet corresponding to the attribute information of the elasticity detection device.

According to the second aspect, and the first, the second, the third, the fourth or the fifth possible implementation form of the second aspect, in a sixth possible implementation form of the second aspect, the data analysis request includes the analysis keyword, the analysis keyword includes at least one of the following information:

individual attribute information of the subject, disease attribute information of the subject, group attribute information of the subject, and attribute information of the elasticity detection device.

According to a third aspect of the present invention, an elasticity detection device is provided. The elasticity detection device includes an excitation device for generating an elastic shear wave in a viscoelastic medium of a subject; a capturing device for obtaining a detection result generated by the viscoelastic medium under an action of the elastic shear wave. The elasticity detection device further includes:

a communication condition determining device, configured to determine whether the communication connection between the elasticity detection device and the cloud server is normal;

a data transceiving device, configured to, transmit the detection result to the cloud server when the communication condition determining device determines that the communication connection is normal, so that the cloud server stores the detection result in the database;

the data transceiving device is further configured to transmit a data analysis request to the cloud server, and the data analysis request is to instruct the cloud server to obtain from the database first data to be analyzed corresponding to an analysis keyword and analyze the first data to be analyzed to obtain a first analysis result; wherein the first data to be analyzed includes a detection result corresponding to the analysis keyword among all detection results of the elasticity detection device;

the data transceiving device is configured to receive and present the first analysis result transmitted by the cloud server.

In a first possible implementation form of the third aspect, the data transceiving device is further configured to: receive an offline data packet transmitted by the cloud server, the offline data packets being determined by the cloud server according to attribute information of the elasticity detection device.

The elasticity detection device further includes: a storage device for storing the offline data packet.

According to the first possible implementation form of the third aspect, in a second possible implementation form of the third aspect, the device further includes:

a data analyzing device, configured to obtain from the offline data packet second data to be analyzed corresponding to the data analysis request and analyze the second data to be analyzed to obtain a second analysis result, the second data to be analyzed including a detection result corresponding to the analysis keyword among all detection results of the elasticity detection device included in the offline data packet.

According to the second possible implementation form of the third aspect, in a third possible implementation form of the third aspect, the data analyzing device is configured to execute the step of obtaining from the offline data packet the second data to be analyzed corresponding to the data analysis request and analyzing the second data to be analyzed to obtain a second analysis result, when the communication condition determining device determines that the communication connection between the elasticity detection device and the cloud server is not normal.

The present invention provides a cloud server including:

a data receiving module for receiving the detection result transmitted by the elasticity detection device, where the detection result is transmitted when it is determined that the communication connection between the elasticity detection device and the cloud server is normal;

a storage processing module for storing the detection result into a database;

where the data receiving module is further used to receive a data analysis request transmitted by the elasticity detection device;

a data analyzing module for obtaining from the database first data to be analyzed corresponding to an analysis keyword according to the data analysis request and analyzing the first data to be analyzed to obtain a first analysis result; where the first data to be analyzed includes a detection result corresponding to the analysis keyword among all detection results of the elasticity detection device;

a data transmitting module for transmitting the first analysis result to the elasticity detection device.

As to the method for data analysis and processing of an elasticity detection device, and the elasticity detection device, each elasticity detection device transmits the detection result to the cloud server so as to be stored in the database, after obtaining the detection result of the viscoelastic medium of the subject and when it is determined that its communication connection to the cloud server is normal, thereby realizing a cloud storage for a detection result of each elasticity detection device. And if the communication connection is normal, then the elasticity detection device may transmit a corresponding data analysis request to the cloud server according to different requirements, and the cloud server obtains the data to be analyzed corresponding to the analysis keyword from the database and analyzes the data to be analyzed to obtain an analysis result that will be transmitted to the elasticity detection device. Thus, the elasticity detection device can not only store its own elasticity detection data in the cloud, but also obtain a more comprehensive data to be analyzed that is directed to the content to be analyzed, i.e., the data corresponding to the keyword to be analyzed, by means of the massive and comprehensive elasticity detection data stored in the cloud server, such as all historical elasticity detection data of each individual. By way of an analysis of the data to be analyzed, it can help to determine the health condition of human body accurately and effectively and provide a reliable support for various researches.

DETAILED DESCRIPTION

In order to make the objectives, technical solutions and advantages of the embodiments of the present invention more clear, the technical solutions of the embodiments of the present invention will be clearly and completely described with reference to the accompanying drawings of the embodiments of the present invention. Obviously, the described embodiments are a part rather than all of the embodiments of the present invention. All other embodiments obtained by those of ordinary skill in the art based on the embodiments of the present invention without creative labor are within the scope of the present invention.

Figure 1:
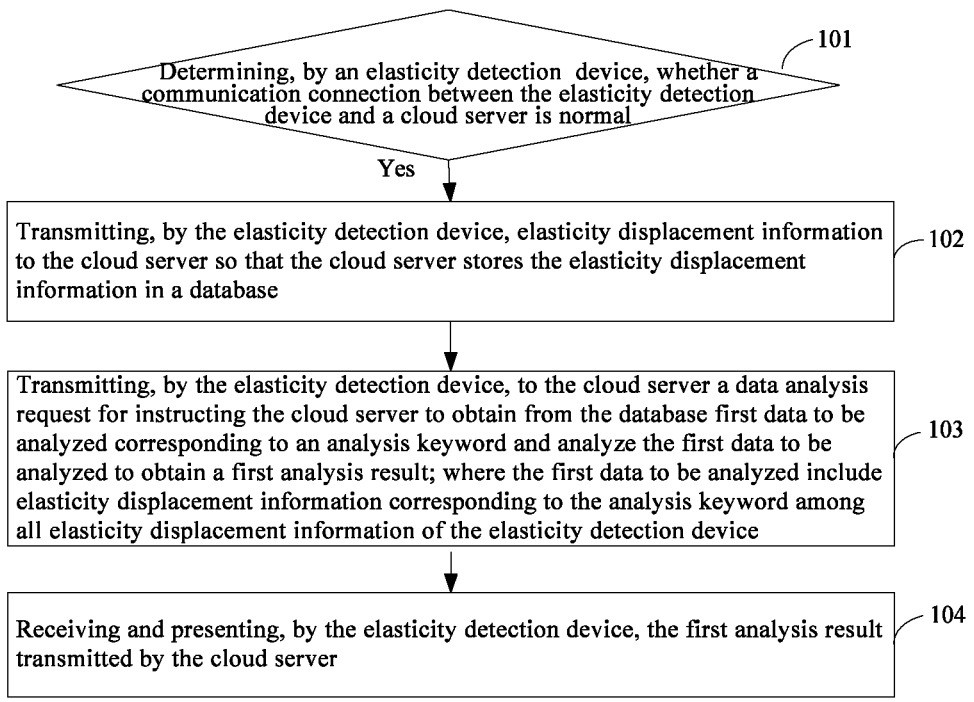
FIG. 1 is a flowchart of a first embodiment of the method for data analysis and processing of the elasticity detection device according to the present invention.

FIG. 1 is a flowchart of a first embodiment of the method for data analysis and processing of the elasticity detection device according to the present invention. In this embodiment, the elasticity detection device includes an excitation device for generating an elastic shear wave in a subject's viscoelastic medium; a capturing device for determining displacement information generated by the viscoelastic medium under an action of the elastic shear wave. The operating principle of the excitation device and the capturing device operate can be simply described as: on a surface of the viscoelastic organ medium such as the liver, a shear wave is excited by the excitation device to the viscoelastic medium, which is equivalent to generating a vibration signal, and the viscoelastic medium vibrates under the vibration signal, and the capturing device may then transmit an ultrasonic signal to the viscoelastic medium which then, according to the principle of elastic mechanic, generates an echo response. Since the elastic stress or elastic strain of the viscoelastic organ medium is different in different states such as normal state or pathological state, the capturing device calculates the displacement of the viscoelastic medium according to echo signals before and after pressing. The displacement information reflects elastic characteristics of the viscoelastic organ and serves as an important reference for human health condition. In this embodiment, different subjects may be detected using different elasticity detection devices at different times, and the following data analysis and processing may be performed by each elasticity detection device after the displacement information of the subject is obtained. As shown in FIG. 1, the method includes:

step 101, determining whether a communication connection between the elasticity detection device and a cloud server is normal, and performing step 102 if the communication connection is normal;

step 102, transmitting, by the elasticity detection device, displacement information to the cloud server so that the cloud server stores the displacement information in a database;

step 103, transmitting, by the elasticity detection device, to the cloud server a data analysis request for instructing the cloud server to obtain first data to be analyzed corresponding to an analysis keyword from the database, and analyze the first data to be analyzed to obtain a first analysis result; wherein the first data to be analyzed includes displacement information corresponding to the analysis keyword among all displacement information of the elasticity detection device;

step 104, receiving and presenting, by the elasticity detection device, the first analysis result transmitted by the cloud server.

It should be noted that, in the present embodiment, the description is only made by taking displacement detection of the viscoelastic medium by the elasticity detection device as an example. However, in practice, the method in the present embodiment can be applied to any one or more detection devices, that is, after obtaining the corresponding detection result, each detecting device performs a cloud data storage of the obtained detection result similarly to what will be described subsequently in the present embodiment, and date analyze can be performed based on the data stored in the cloud. In addition, as described above, when the capturing device performs the detection, the displacement of the viscoelastic organ medium is obtained according to the difference in the elastic stress or elastic strain of the viscoelastic organ medium in different states. It is obvious that the capturing device can also be used to obtain the strain and other motion parameters of the viscoelastic organ medium.

When the elasticity detection device is used to examine a certain subject, the subject's displacement information is obtained, and the displacement information includes, for example, individual attribute information such as name, age, identification number, and contact information of the subject, and the displacement obtained by detection. It may also include, for example, identification information of the elasticity detection device, information of the hospital where the elasticity detection device is located, information of the doctor who operates the elasticity detection device, and the like.

In the present embodiment, in order to help medical personnel to obtain a more comprehensive medical history information of the subject so as to provide a comprehensive and accurate assessment of the health condition of the subject; or in order to help relevant researchers to conduct a comprehensive analysis of a certain type of disease or a targeted analysis of disease characteristics of the population with certain disease characteristics; or in order to help researchers to analyze national or regional epidemics, etc., the cloud server is introduced, thus it is possible to obtain a comprehensive analysis result of detection data for e.g., a certain individual, a certain group of people, or a certain type of disease through the currently used elasticity detection device by means of storage and analysis capabilites of the cloud server on massive data.

Specifically, the elasticity detection device first determines whether the communication connection between itself and the cloud server is normal after detecting and obtaining the displacement information of a certain subject detected by using the device. The connection between the elasticity detection device and the cloud server may be, for example, a wired connection or a wireless network connection such as WLAN, 3G, 4G or GRPS, and is not particularly limited. That is, the elasticity detection device is configured to have a communication function. The communication connection being normal is that it can be connected to the network, or the network signal strength is greater than a preset threshold, etc.

After determining that the communication connection between the elasticity detection device and the cloud server is normal, the elasticity detection device can, on one hand, upload the obtained displacement information to the cloud server for storage, thereby reducing the requirement for the storage capacity of the elasticity detection device, and on the other hand, the elasticity detection device can transmit a data analysis request to the cloud server to obtain a comprehensive and accurate analysis result for a certain analysis requirement performed by medical personnel, researchers or other relevant personnel. Where the data analysis request is used to instruct the cloud server to obtain from the database first data to be analyzed corresponding to the analysis keyword and analyze the first data to be analyzed to obtain a first analysis result. The analysis keyword can be a default setting, or vary according to an actual requirement. Specifically, the analysis keyword may be carried in the data analysis request, and may include at least one of the following information: individual attribute information of the subject, disease attribute information of the subject, group attribute information of the subject, and attribute information of the elasticity detection device. Specifically, the disease attribute information of the subject is, for example, name of a certain disease; the group attribute information of the subject may be, for example, age, sex, place of residence, and the like; the attribute information of the elasticity detection device may be, for example, an identification of a hospital in which the device is located, an identification of an area in which the device is located, an identification of a body parameter for detection, and the like. For example, if medical personnel want to know about the current subject's historical elasticity detection result of liver, i.e., historical displacement information of liver so as to make an accurate judgment and tracking for the health conditions of the liver, and at this point, the analysis keyword may be the individual attribute information of the subject such as name, age, and identification number. For another example, if the researchers want to know distribution characteristic of a certain type of disease, such as a region where the disease is mainly distributed and a population in which the disease is mainly distributed, then the analysis keyword can only include the identification information of the disease. For yet another example, if the researchers want to know disease characteristics of a certain type of patient, such as analysis result of a disease to which the population in a same age group, or located in a same region are susceptible, then the analysis keyword is group attribute information of the subject. Further, the analysis keyword may also be attribute information of the elasticity detection device, such as a device identification, so that the usage of the elasticity detection device can be known according to the analysis of the total amount of the detection data detected by using the device. In addition, in the case where many hospitals upload elasticity detection results, i.e., all displacement information, to the cloud server and the information is shared, the analysis keyword may further include, for example, information such as hospital identification or doctor identification or the like.

After receiving the data analysis request transmitted by the elasticity detection device, the cloud server queries and obtains from its own database the matched data to be analyzed according to the analysis keyword. For example, if the analysis keyword is body attribute information of the subject, the data to be analyzed is all displacement information of the subject, that is, all displacement information of the elasticity detection performed on the subject using each elasticity detection device. Thus, the analysis of the data to be analyzed can realize the tracking of the subject's detection record and determine the health condition reflected by the elasticity detection result, so that a comprehensive and accurate analysis result is obtained. For yet another example, if the analysis keyword is an identification of a certain type of disease, then the data to be analyzed is the detection data that is obtained from all the people on whom the detection for this type of disease is performed and meets certain requirements. Thus, a predicted result of the disease in the national or region can be obtained by a comprehensive analysis of the age, sex, place of residence, occupation, etc., of all the people on whom the detection for this type of disease is performed. It should be noted that, in the case that in the present embodiment the elasticity detection is taken as an example, the disease mentioned above particularly refers to a disease associated with the elasticity detection result. Thus, the displacement information included in the data to be analyzed corresponding to the disease needs to meet the requirements corresponding to the disease, for example, in the case of A disease, the displacement is generally within the range of a1-a2; and in case of B disease, the displacement is generally within the range of b1-b2.

Finally, after the elasticity detection device receives the analysis result as a feedback from cloud server, the analysis result can be presented on the elasticity detection device by ways of words, graphs, such as a trend chart of detection results of a certain individual's historical displacement, and the like.

In the present embodiment, each elasticity detection device obtains the subject's displacement information, and transmits the displacement information to the cloud server if its communication connection to the cloud server is determined to be normal, so that the cloud server stores the displacement information in the database. Based on this, i.e., the fact that the cloud server stores a large number of elasticity detection results, if the communication connection between the elasticity detection device and the cloud server is normal, the elasticity detection device can transmit data analysis requests for different requirements to the cloud server. The cloud server obtains from the database the data to be analyzed corresponding to the analysis keyword and analyzes the data to be analyzed to obtain an analysis result, and transmits the analysis result to the elasticity detection device. Thus, the elasticity detection device can not only store its own detection result in the cloud, but also obtain more comprehensive data to be analyzed corresponding to a keyword to be analyzed by means of massive and comprehensive detection result information stored in the cloud server. By analysis of the data to be analyzed, a comprehensive and accurate analysis result can be obtained, which helps to accurately and effectively determine a health condition of a human body and provides a reliable support for various researches.

Figure 2:
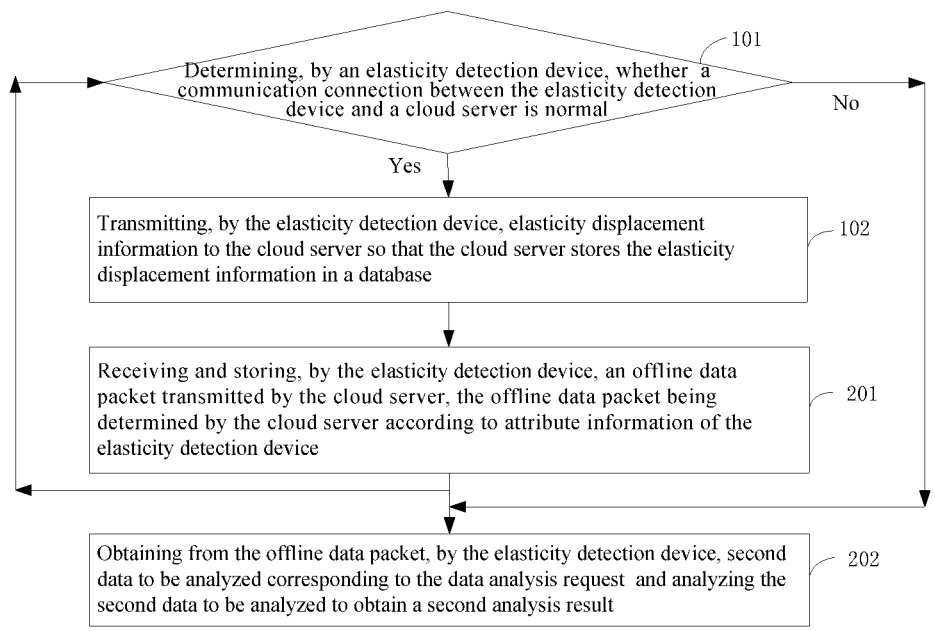
FIG. 2 is a flowchart of a second embodiment of the method for data analysis and processing of the elasticity detection device according to the present invention.

FIG. 2 is a flowchart of a second embodiment of the method for data analysis and processing of the elasticity detection device according to the present invention. As shown in FIG. 2, on the basis of the embodiment shown in FIG. 1, after it is determined that the communication connection between the elasticity detection device and the cloud server is normal, optionally, the following steps 201-202 may be included.

Step 201, receiving and storing, by the elasticity detection device, an offline data packet transmitted by the cloud server, the offline data packets being determined by the cloud server according to attribute information of the elasticity detection device.

Step 202, obtaining, by the elasticity detection device, second data to be analyzed corresponding to the data analysis request, from the offline data packet and analyzing the second data to be analyzed to obtain a second analysis result.

In the present embodiment, an offline data packet mechanism is used in order to obtain, by the elasticity detection device, a relatively complete and accurate analysis result when the communication connection between the elasticity detection device and the cloud server is not normal, that is, the elasticity detection device cannot be connected to the cloud server or communication quality between the elasticity detection device and the cloud server is poor.

Specifically, after determining that the communication connection between the elasticity detection device and the cloud server is normal, the elasticity detection device can also receive and store the offline data packet transmitted by the cloud server, wherein the offline data packet are determined by the cloud server according to the attribute information of the elasticity detection device. Specifically, the elasticity detection device can obtain an offline data packet corresponding to its own attribute information as follows.

The elasticity detection device may transmit to the cloud server an offline packet download request, wherein the download request includes attribute information of the elasticity detection device. The attribute information of the elasticity detection device may include, for example, various information listed above, such as an identification of an area where the elasticity detection device is located. Therefore, after receiving the download request, the cloud server can obtain from its own database all detection results corresponding to the attribute information of the elasticity detection device, i.e., all displacement information corresponding to the attribute information, and pack the displacement information into an offline data packet, then transmit the offline data packet to the elasticity detection device so that the elasticity detection device locally stores the offline data packet.

It should be noted that the way that the above elasticity detection device requests the cloud server to generate the offline data packet based on the attribute information is used in order to enable the elasticity detection device to obtain the data needed by itself and have better pertinence. Of course, the way that the cloud server by itself generates different offline data packets according to a preset rule for the elasticity detection device to passively select can also be used. In addition, in order to guarantee the real-time validity of the offline data packet stored in the elasticity detection device, the cloud server can use a periodically updated strategy to periodically update the offline data packet required by the elasticity detection device, and thus periodically transmit the updated offline data packet to the elasticity detection device so as to enable the elasticity detection device to periodically update the locally stored offline data packet.

Further, in the case where the elasticity detection device locally stores the offline data packet transmitted from the cloud server, if the communication connection between the elasticity detection device and the cloud server is normal, the elasticity detection device can obtain not only the first analysis result from the cloud server but also the second analysis result from the offline data packet. Furthermore, the second analysis result mentioned above can be obtained from the offline data packet if it is determined that the communication connection between the elasticity detection device and the cloud server is not normal.

In the present embodiment, if it is determined that the communication connection between the elasticity detection device and the cloud server is not normal, such as network failure, too low signal strength, the elasticity detection device can perform data analysis based on the offline data packet locally stored, that is, obtaining from the locally stored offline data packet the data to be analyzed corresponding to the data analysis request and obtaining a analysis result by analyzing the data to be analyzed. The specific analysis process is similar to the analysis through the database of the cloud server, except that the database used at this point is the offline data packet locally stored. Thus details of the process will not be described here.

In the present embodiment, if the communication connection between the elasticity detection device and the cloud server is not normal, the elasticity detection device can perform data analysis using the offline data packet that is directed to the elasticity detection device and is received from the cloud server when the communication connection is normal. Since displacement information included in the offline data packet of a certain elasticity detection device includes not only historical displacement information detected using the elasticity detection device, but also historical displacement information uploaded by other elasticity detection device to the cloud server, that is, the data in the offline data packet are the latest and relatively comprehensive data which is specific for the certain elasticity detection device, the analysis results obtained by using the offline data packet are also relatively comprehensive and accurate.

Figure 3:
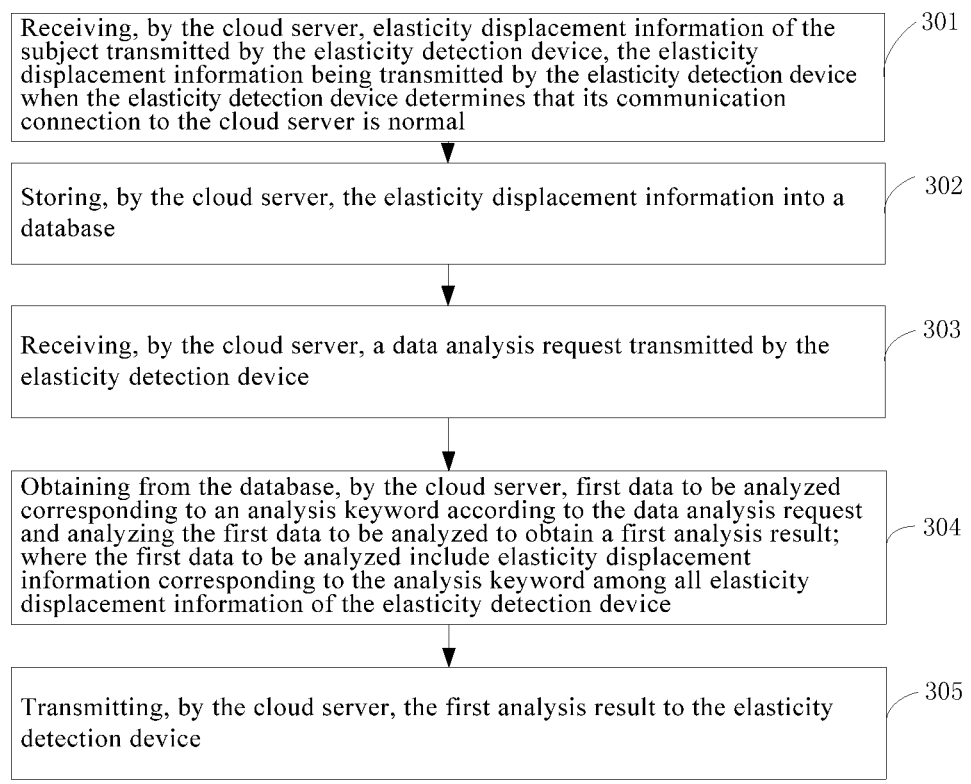
FIG. 3 is a flowchart of a third embodiment of the method for data analysis and processing of the elasticity detection device according to the present invention.

FIG. 3 is a flowchart of a third embodiment of the method for data analysis and processing of the elasticity detection device according to the present invention. As shown in FIG. 3, the method is executed by a cloud server, and specifically includes:

step 301, receiving, by the cloud server, displacement information of a subject transmitted by the elasticity detection device, the displacement information being transmitted by when it is determined that communication connection between the elasticity detection device and the cloud server is normal;

step 302, storing, by the cloud server, the displacement information into a database;

step 303, receiving, by the cloud server, a data analysis request transmitted by the elasticity detection device;

step 304, obtaining from the database, by the cloud server, first data to be analyzed corresponding to an analysis keyword according to the data analysis request and analyzing the first data to be analyzed to obtain a first analysis result; where the first data to be analyzed includes displacement information corresponding to the analysis keyword among all displacement information of the elasticity detection device; and step 305, transmitting, by the cloud server, the first analysis result to the elasticity detection device.

Specifically, the displacement information can be obtained by medical personnel using the elasticity detection device to perform elasticity detection on a viscoelastic organ medium, such as a human liver. The displacement information includes, for example, individual attribute information of the subject, such as name, age, identification number, and contact information, and may also include attribute information of the elasticity detection device such as device identification, and information of a doctor who performs the detection and hospital information.

On one hand, in order to reduce the requirement for the storage capacity of the elasticity detection device, and on the other hand, in order to enable relevant personnel such as a doctor to obtain a more comprehensive data analysis result through the elasticity detection device, each elasticity detection device in the present embodiment uploads the displacement information obtained to the cloud server for storage if the communication connection between the each elasticity detection device and the cloud server is normal, so that the cloud server to store comprehensive and massive detection results, which is conducive to a comprehensive data analysis of a certain subject, certain group of people, certain disease or the like.

Therefore, if it is determined that communication connection between the elasticity detection device and the cloud server is normal, the elasticity detection device uploads the displacement information to the cloud server, and the cloud server receives the displacement information transmitted from the elasticity detection device and stores it in a database. It is understood that the elasticity detection device also stores locally displacement information of the subject obtained by detections.

Specifically, storage of displacement information in the cloud server can be, for example, classified storage, such as establishing different databases or partitioning one database into different storing spaces, according to different hospitals or areas; or can be classified storage according to an identification of a certain type of disease where displacement information of a same disease of a same subject in the storage process is stored collectively so as to improve storage efficiency and facilitate the subsequent data query. Of course, the displacement information can also be stored collectively according to time order.

After determining that the communication connection to the cloud server is normal, the elasticity detection device can send a data analysis request to the cloud server, and the cloud server obtains a comprehensive and accurate analysis result directed to an analysis keyword according to the data analysis request. The data analysis request may carry the analysis keyword and the analysis keyword includes at least one of the followings: individual attribute information of the subject, disease attribute information of the subject, group attribute information of the subject, and attribute information of the elasticity detection device. The meaning of each of the above information has been described in detail in the embodiment shown in FIG. 1 and will not be described again here.

After receiving the data analysis request sent by the elasticity detection device, the cloud server queries and obtains the data to be analyzed, which is matches the analysis keyword, from the database according to the data analysis request, where the analysis keyword, for example, is the human body attribute information of the subject, and the data to be analyzed is all displacement information of the subject, that is, all displacement information of the elasticity detection performed on the subject by each elasticity detection device. Thus, the analysis of the data to be analyzed can achieve detection record tracking of the subject and determine the health condition reflected by the elasticity detection result, so that a comprehensive and accurate analysis result is obtained. For another example, if the analysis keyword is an identification of a certain type of disease, then the data to be analyzed is the detection data that is obtained from all the people on whom the detection for this type of disease is performed and meets certain requirements. Thus, a predicted result of the disease in the national or region can be obtained by a comprehensive analysis of the age, sex, place of residence, occupation, etc., of all the people on whom the detection for this type of disease is performed. In addition, the analysis result may include, for example, medical history, impact factor, diagnosis and treatment reports, and the like. And a secondary analysis can also be performed based on these analyzed data to obtain additional data on result data, such as disease correlation, medical intervention, etc.

In the present embodiment, if the communication connection between the elasticity detection device and the cloud server is normal, the elasticity detection device can transmit a data analysis request to the cloud server. The cloud server obtains from a database the data to be analyzed corresponding to a analysis keyword and analyzes the data to be analyzed for a certain subject, certain group of people, certain type of disease, certain device or the like to obtain an analysis result. Thus, the relevant personnel such as doctors, researchers and so on can achieve big data analysis for different analysis requirements by means of massive and comprehensive detection result information stored in the cloud server, so as to obtain comprehensive and accurate analysis results on the side of elasticity detection device.

Figure 4:
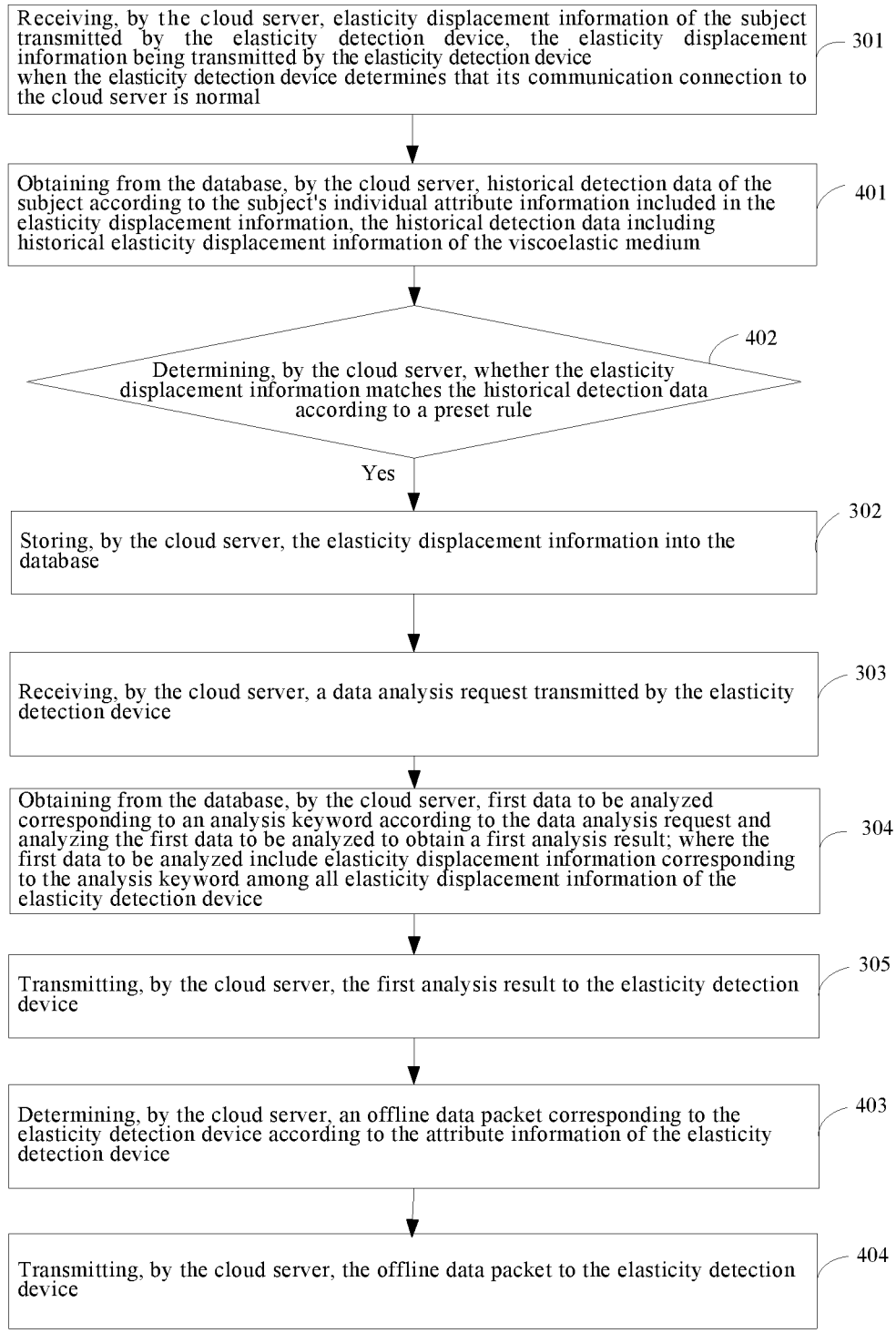
FIG. 4 is a flowchart of a fourth embodiment of the method for data analysis and processing of the elasticity detection device according to the present invention.

FIG. 4 is a flowchart of a fourth embodiment of the method for data analysis and processing of the elasticity detection device according to the present invention. As shown in FIG. 4, on the basis of the embodiment shown in FIG. 3, before the cloud server stores the displacement information into a database in step 302, the method may further include the following steps:

step 401, obtaining from the database, by the cloud server, historical detection data of the subject according to the subject's individual attribute information included in the displacement information, wherein the historical detection data include historical displacement information of the viscoelastic medium;

step 402, determining, by the cloud server, whether the displacement information matches the historical detection data according to a preset rule.

If a certain elasticity detection device only detects displacement information of the subject, the subject's health condition reflected by the displacement information may not conform with the actual situation. Therefore, a data correction mechanism is provided in this embodiment to guarantee the accuracy of the displacement information stored in the cloud server.

Specifically, after receiving the displacement information transmitted from each elasticity detection device, the cloud server firstly determines the matching of the displacement information and the subject's historical detection data. Specifically, the cloud server firstly extracts the individual attribute information of the subject such as the name and the identification number from the displacement information, and then obtains from the database historical detection data corresponding to the individual attribute information, where the historical detection data include both the subject's historical displacement information and historical detection results of other physical parameters other than the elasticity of the viscoelastic medium. Thereafter, the cloud server determines whether the subject's current displacement information matches his historical detection data. If they match, step 302 is executed: storing, by the cloud server, the current displacement information into a database; If they do not match, step 302 will be changed as: storing, by the cloud server, the current displacement information into a database, correcting the current displacement information according to the historical detection data, and storing corrected displacement information in the database. The determining of matching, for example, may be to determine whether a correction is required according to, for example, two adjacent displacement values, and if the difference between two sequentially obtained displacement values of the subject is less than a preset threshold, then no correction is required, i.e., the matching requirement is met; on the contrary, if the difference is greater than the preset threshold, for example, if the previous displacement value is 10, and the current detected displacement value is 20, and the difference therebetween is greater than a threshold, e.g., 5, then a correction process is required. In fact, it is likely that due to the subject is currently suffering from other disease, such as inflammation, there is a great change in the displacement value. However, the great change is caused by the inflammation and does no indicate that the subject has a serious problem in organ elasticity. Therefore, when it is determined that there is a factor affecting the current displacement information in the historical detection data, the current displacement information can be corrected through an elasticity normal model of the viscoelastic medium, which model is obtained by pre-statistic, in combination with the historical displacement information of the subject. For example, the current displacement information is corrected according to value range of the normal model in which the overall trend of the historical displacement value of the subject is located so that the corrected displacement value is in a range corresponding to the normal model. Furthermore, the cloud server feeds back a prompt message to the elasticity detection device to indicate that the current displacement information does not match the historical detection data, so that an operator of elasticity detection device, such as a doctor, makes an accurate judgment on the health condition reflected by the subject's currently detected displacement information.

In addition, it should be noted that there is another case where although the currently detected displacement information differs greatly from the historical displacement information, such as the previously adjacent displacement value, it is determined by analysis of the cloud server that in the subject's other historical detection data, that is, in detection parameters other than the elasticity, there is no factor that affects and greatly changes the current detection result of the elasticity detection. In this case, it is likely that there is a wrong operation during detection, and at this time, the cloud server can send an instruction message to the elasticity detection device, prompting that the current displacement information does not match the historical detection data, and the elasticity detection device can perform a redetection according to the instruction.

Further, the method may further include:

step 403, determining, by the cloud server, an offline data packet corresponding to the elasticity detection device according to the attribute information of the elasticity detection device;

step 404, transmitting, by the cloud server, the offline data packet to the elasticity detection device.

Here, the offline data packet is used to make the elasticity detection device obtain from the offline data packet a second data to be analyzed corresponding to a data analysis request and analyze the second data to be analyzed to obtain a second analysis result, where the second data to be analyzed include displacement information corresponding to the analysis keyword among all displacement information of the elasticity detection device included in the offline data packet.

It should be noted that the above steps 403-404 may be performed after step 305, which is only an optional way and is not limited by this example.

Specifically, in step 403, the determining, by the cloud server, an offline data packet corresponding to the elasticity detection device according to the attribute information of the elasticity detection device can be realized by the following way:

receiving, by the cloud server, a request for downloading the offline data packet transmitted by the elasticity detection device, the download request including attribute information of the elasticity detection device; generating, by the cloud server, an offline data packet corresponding to the attribute information of the elasticity detection device.

Specifically, after determining the communication connection to the cloud server is normal, the elasticity detection device transmits an offline packet download request to the cloud server, where the download request includes attribute information of the elasticity detection device. The attribute information of the elasticity detection device may include, for example, an identification of the area where the elasticity detection device is located. Therefore, after receiving the download request, the cloud server can query and obtain from the database all detection results corresponding to the attribute information of the elasticity detection device, i.e., all displacement information of the elasticity detection device corresponding to the attribute information, from its own database, and pack the displacement information into an offline data packet, then the transmit offline data packet to the elasticity detection device.

In addition, the cloud server may determine the offline data packet corresponding to the elasticity detection device by the following way:

determining, by the cloud server, whether there is identification information matching the attribute information of the elasticity detection device, among the identification information of at least one offline data packet generated in advance; if there is, then obtaining, by the cloud server, an offline data packet corresponding to the matched identification information, and transmitting the offline data packet to the elasticity detection device.

In the present embodiment, the cloud server can classify massive displacement information stored therein in advance, for example, according to areas, or disease, i.e., disease identification. Thus, each class corresponds to a class of offline data packets, and each class of offline data packets is marked with corresponding identification information. Since the cloud server stores the attribute information of each elasticity detection device, the cloud server can initiatively transmit to the elasticity detection device an offline data packet corresponding to the attribute information of the elasticity detection device. In an specific implementation, the cloud server can query whether the elasticity detection device needs the offline data packet by way of request response, In addition, in order to guarantee real-time validity of the offline data packet stored in the elasticity detection device, the cloud server can periodically update the offline data packet required by the elasticity detection device using a periodically updated strategy, to guarantee the real-time of the offline data packet stored in the elasticity detection device.

In the present embodiment, an offline packet mechanism is used, and when the communication connection between the elasticity detection device and the cloud server is normal, the elasticity detection device downloads the offline data packet, so that data analysis directed to an data analysis request can be performed to obtain a comprehensive and accurate analysis result, based on the displacement information in the offline packet or the displacement information stored in the cloud server. If the communication connection is not normal, the elasticity detection device can obtain a relatively comprehensive and accurate analysis result by using the offline data packet as the database. It should be noted that when the communication connection is normal, if the elasticity detection device selects to obtain the analysis result by the offline data packet, then it is a compromise between accuracy and real-time because although the analysis result by the cloud server is more accurate, it takes a relatively longer time whereas although the analysis result by the offline data packet stored locally is relatively poor, it has better real-time.

Figure 5:
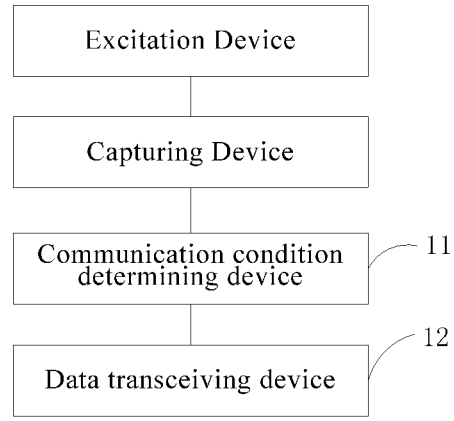
FIG. 5 is a schematic diagram of the structure of a first embodiment of the elasticity detection device according to the present invention.

FIG. 5 is a schematic diagram of the structure of a first embodiment of the elasticity detection device according to the present invention. The elasticity detection device includes an excitation device for generating an elastic shear wave in a subject's viscoelastic medium; and a capturing device for determining displacement information generated by the viscoelastic medium under an action of the elastic shear wave. In addition, as shown in FIG. 5, the elasticity detection device further includes:

a communication condition determining device 11, configured to determine whether communication connection between the elasticity detection device and the cloud server is normal;

a data transceiving device 12, configured to transmit the displacement information to the cloud server so that the cloud server stores the displacement information in a database when the communication condition determining device 11 determines that the communication connection is normal;

the data transceiving device 12 is further configured to transmit to the cloud server a data analysis request for instructing the cloud server to obtain from the database first data to be analyzed corresponding to an analysis keyword and analyze the first data to be analyzed to obtain a first analysis result; where the first data to be analyzed includes displacement information corresponding to the analysis keyword among all displacement information of the elasticity detection device;

the data transceiving device 12 is configured to receive and present the first analysis result transmitted by the cloud server.

Where the data analysis request includes the analysis keyword, and the analysis keyword includes at least one of the followings:

individual attribute information of the subject, disease attribute information of the subject, group attribute information of the subject, and attribute information of the elasticity detection device.

The elasticity detection device provided by the present embodiment can be configured to execute the method of the embodiment shown in FIG. 1, and the basic principle and technical effect thereof are similar to the embodiment shown in FIG. 1, and thus will not be repeated here.

Figure 6:
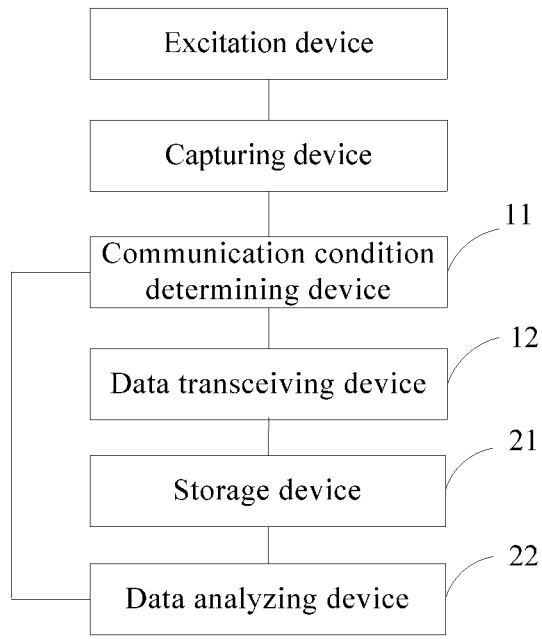
FIG. 6 is a schematic diagram of the structure of a second embodiment of the elasticity detection device according to the present invention.

FIG. 6 is a schematic diagram of the structure of a second embodiment of the elasticity detection device according to the present invention. As shown in FIG. 6, the elasticity detection device is based on the embodiment shown in FIG. 5, and the data transceiving device 12 is further configured to: receive the offline data packet transmitted by the cloud server, where the offline data packet is determined by the cloud server according to the attribute information of the elasticity detection device;

the elasticity detection device further includes: a storage device 21 for storing the offline data packet.

Further, the elasticity detection device further includes: a data analyzing device 22, configured to obtain from the offline data packet second data to be analyzed corresponding to the data analysis request and analyze the second data to be analyzed to obtain a second analysis result, where the second data to be analyzed include displacement information corresponding to the analysis keyword among all displacement information of the elasticity detection device included in the offline data packet.

The data analyzing device 22 is configured to execute the step of obtaining from the offline data packet the second data to be analyzed corresponding to the data analysis request and analyzing the second data to be analyzed to obtain the second analysis result if the communication condition determining device determines that the communication connection between the elasticity detection device and the cloud server is not normal.

The elasticity detection device provided by the present embodiment can be used to execute the method of the embodiment shown in FIG. 2, and the basic principle and the technical effect thereof are similar to the embodiment shown in FIG. 2 and thus will not be repeated here.

Figure 7:
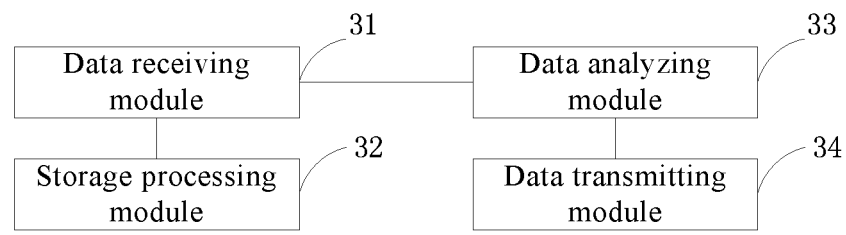
FIG. 7 is a schematic diagram of the structure of a first embodiment of the cloud server according to the present invention.

FIG. 7 is a schematic diagram of the structure of a first embodiment of the cloud server according to the present invention. As shown in FIG. 7, the cloud server includes:

a data receiving module 31 for receiving displacement information of the subject transmitted by the elasticity detection device, where the displacement information is transmitted when it is determined that the communication connection between the elasticity detection device and the cloud server is normal;

a storage processing module 32 for storing the displacement information in a database;

where the data receiving module 31 is further used to receive a data analysis request transmitted by the elasticity detection device;

a data analyzing module 33 for obtaining from the database first data to be analyzed corresponding to an analysis keyword according to a data analysis request and analyzing the first data to be analyzed to obtain a first analysis result; where the first data to be analyzed includes displacement information corresponding to the analysis keyword among all displacement information of the elasticity detection device;

a data transmitting module 34 for transmitting the first analysis result to the elasticity detection device.

The cloud server provided by the present embodiment can be used to execute the method of the embodiment shown in FIG. 3, and the basic principle and the technical effect thereof are similar to the embodiment shown in FIG. 3 and thus will not be repeated here.

Figure 8:
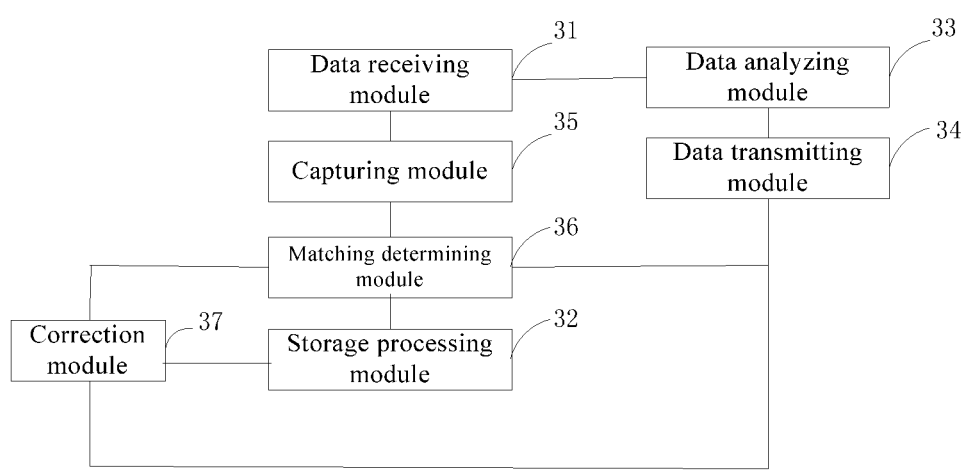
FIG. 8 is a schematic diagram of the structure of a second embodiment of the cloud server according to the present invention.

FIG. 8 is a schematic diagram of the structure of a second embodiment of the cloud server according to the present invention. As shown in FIG. 8, the cloud server, on the basis of the embodiment shown in FIG. 7, further includes:

a obtaining module 35 for obtaining historical detection data of the subject from the database according to the subject's individual attribute information included in the displacement information, where the historical detection data include historical displacement information of the viscoelastic medium;

a matching determining module 36 for determining whether the displacement information matches the historical detection data according to a preset rule.

Further, the cloud server further includes: a correction module 37 for correcting the displacement information according to the historical detection data if the displacement information does not match the historical detection data;

the storage processing module 32 is specifically used to store the corrected displacement information in the database;

the data transmitting module 34 is further used to feed back a prompt message to the elasticity detection device, the prompt message is used for prompting that the displacement information does not match the historical detection data.

Furthermore, the obtaining module 35 is further used to determine the offline data packet corresponding to the elasticity detection device according to the attribute information of the elasticity detection device;

the data transmitting module 34 is further used to transmit the offline data packet to the elasticity detection device; the offline data packet are used so that the elasticity detection device can obtain from the offline data packet second data to be analyzed corresponding to the data analysis request and analyze the second data to be analyzed to obtain a second analysis result, where the second data to be analyzed include displacement information corresponding to the analysis keyword among all displacement information of the elasticity detection device included in the offline data packet.

Further, the obtaining module 35 is specifically used to:

determine identification information matching the attribute information of the elasticity detection device among identification information of at least one offline data packet generated in advance;

obtain an offline data packet corresponding to the matched identification information.

Furthermore, the data receiving module 31 is used to receive an offline data packet download request transmitted by the elasticity detection device, where the download request includes attribute information of the elasticity detection device;

the obtaining module 35 is further used to generate the offline data packet corresponding to the attribute information of the elasticity detection device.

The cloud server provided by the present embodiment can be used to execute the method of the embodiment shown in FIG. 4, and the basic principle and the technical effect thereof are similar to the embodiment shown in FIG. 4 and thus will not be repeated here.

In the above embodiments of the present invention, the detection result uploaded to the cloud server is described by taking the displacement as an example. However, in other embodiments the detection result uploaded to the cloud server may also be other motion parameters such as strain, which may be designed according to actual needs, and the present invention is not limited thereto.

Finally, it should be understood that the above embodiments are merely to illustrate technical solutions of the present invention and are not to be limiting; while the present invention has been described in detail with reference to the foregoing embodiments, it will be understood by those skilled in the art that modifications may be made to the technical solutions described in the foregoing embodiments or equivalent substitutions may be made to some or all of the technical features therein; and such modifications and substitutions do not make the essence of the corresponding technical solutions depart from the scope of the technical solutions of the embodiments of the present invention.

What is claimed is:

1. A method for medical data analysis and processing of an elasticity detection device, the elasticity detection device comprising an excitation device for generating an elastic shear wave in a subject's viscoelastic medium, and a capturing device for determining displacement information generated by the viscoelastic medium of a human body under an action of the elastic shear wave; wherein the method for medical data analysis and processing of an elasticity detection device comprises:

determining, by the elasticity detection device, whether a communication connection between the elasticity detection device and a cloud server is normal;

when the communication connection is normal, transmitting, by the elasticity detection device, the displacement information to the cloud server so that the cloud server stores the displacement information into a medical database of the cloud server;

receiving and storing, by the elasticity detection device, an offline medical data packet of the human body transmitted by the cloud server, the offline medical data packet of the human body being determined by the cloud server according to attribute information of the elasticity detection device, wherein the offline medical data packet of the human body is periodically updated by the elasticity detection device according to the offline medical data packet of the human body transmitted by the cloud server so as to guarantee the real-time validity of the offline medical data packet and is stored in the elasticity detection device;

transmitting, by the elasticity detection device, to the cloud server a medical data analysis request comprising an analysis keyword so as to instruct the cloud server to obtain from the medical database first medical data of the human body to be analyzed corresponding to the analysis keyword, and analyze the first medical data of the human body to be analyzed to obtain a first analysis result for determining health condition of the human body; wherein the first medical data of the human body to be analyzed comprise displacement information corresponding to the analysis keyword among all displacement information of the elasticity detection device; and receiving and presenting, by the elasticity detection device, the first analysis result transmitted by the cloud server;

when the elasticity detection device determines that the communication connection between the elasticity detection device and the cloud server is not normal, obtaining from the offline medical data packet of the human body, by the elasticity detection device, second medical data of the human body to be analyzed corresponding to the medical data analysis request and analyzing the second medical data of the human body to be analyzed to obtain a second analysis result for determining health condition of the human body, wherein the first analysis result and the second analysis result are presented on the elasticity detection device by ways of a trend chart of detection results of the human body's historical displacement, and wherein the second medical data of the human body to be analyzed comprise displacement information corresponding to the analysis keyword among all displacement information of the elasticity detection device comprised in the offline medical data packet of the human body.

2. The method according to claim 1, wherein the analysis keyword comprises at least one of the followings:

individual attribute information of the subject, disease attribute information of the subject, group attribute information of the subject, and attribute information of the elasticity detection device.

3. The method according to claim 2, wherein the disease attribute information of the subject is a name of a certain disease, the group attribute information of the subject is an age, a sex, a place of residence, the attribute information of the elasticity detection device is an identification of a hospital in which the device is located, an identification of an area in which the device is located, an identification of a body parameter for detection.

4. The method according to claim 2, wherein, the method further comprises:

uploading, by multiple elasticity detection devices from multiple hospitals, the first medical analysis result and the second medical analysis result to the multiple hospitals so that the first analysis medical result and the second analysis medical result are shared by the multiple hospitals, and wherein the analysis keyword further comprises a hospital identification or a doctor identification.

5. The method according to claim 1, wherein the storage of displacement information into the medical database the cloud server is a classified storage that establishing different medical databases or partitioning one medical database into different storing spaces according to different hospitals or areas, or is a classified storage according to an identification of a certain type of disease where displacement information of a same disease of a same subject in a storage process is stored collectively so as to improve storage efficiency and facilitate the subsequent data query.

6. An elasticity detection device comprising an excitation device for generating an elastic shear wave in a subject's viscoelastic medium, and a capturing device for determining displacement information generated by the viscoelastic medium of a human body under an action of the elastic shear wave; wherein the elasticity detection device further comprises:

a communication condition determining device configured to determine whether a communication connection between the elasticity detection device and a cloud server is normal;

a data transceiving device configured to transmit the displacement information to the cloud server when the communication condition determining device determines that the communication connection is normal, so that the cloud server stores the displacement information into a medical database of the cloud server, wherein the data transceiving device is further configured to receive an offline medical data packet of the human body transmitted by the cloud server, the offline medical data packet of the human body being determined by the cloud server according to attribute information of the elasticity detection device, wherein the offline medical data packet of the human body is periodically updated by the elasticity detection device according to the offline medical data packet of the human body transmitted by the cloud server so as to guarantee the real-time validity of the offline medical data packet and is stored in the elasticity detection device;

the data transceiving device is further configured to transmit to the cloud server a medical data analysis request comprising an analysis keyword so as to instruct the cloud server to obtain from the medical database first medical data of the human body to be analyzed corresponding to the analysis keyword and analyze the first medical data of the human body to be analyzed to obtain a first analysis result for determining health condition of the human body; wherein the first medical data of the human body to be analyzed comprises displacement information corresponding to the analysis keyword among all displacement information of the elasticity detection device; and the data transceiving device is further configured to receive and present the first analysis result transmitted by the cloud server;

a storage device configured to store the offline medical data packet of the human body;

a data analyzing device configured to obtain from the offline medical data packet of the human body second medical data of the human body to be analyzed corresponding to the medical data analysis request and analyze the second medical data of the human body to be analyzed to obtain a second analysis result for determining health condition of the human body when the communication condition determining device determines that the communication connection between the elasticity detection device and the cloud server is not normal, wherein the first analysis result and the second analysis result are presented on the elasticity detection device by ways of a trend chart of detection results of the human body's historical displacement, and wherein the second medical data of the human body to be analyzed comprise displacement information corresponding to the analysis keyword among all displacement information of the elasticity detection device comprised in the offline medical data packet of the human body.

7. The device according to claim 6, wherein the displacement information comprises a name of a certain disease, an age, a sex, a place of residence, an identification of a hospital in which the device is located, an identification of an area in which the device is located, and an identification of a body parameter for detection.

8. The device according to claim 6, wherein the first medical analysis result and the second medical analysis result are uploaded to multiple hospitals so that the first medical analysis result and the second medical analysis result are shared by the multiple hospitals, and wherein the displacement information further comprises a hospital identification or a doctor identification.

9. The device according to claim 6, wherein the storage of displacement information into the medical database of the cloud server is a classified storage that establishing different medical databases or partitioning one medical database into different storing spaces according to different hospitals or areas, or is a classified storage according to an identification of a certain type of disease where displacement information of a same disease of a same subject in a storage process is stored collectively so as to improve storage efficiency and facilitate the subsequent data query.

* * * * *